(12) United States Patent
Kwok et al.

(10) Patent No.: US 9,328,133 B2
(45) Date of Patent: *May 3, 2016

(54) FERRIC ORGANIC COMPOUNDS, USES THEREOF AND METHODS OF MAKING SAME

(71) Applicant: Panion & BF Biotech, Inc., Taipei (TW)

(72) Inventors: David W. K. Kwok, Vancouver (CA); Nikolay Mintchev Stoynov, Vancouver (CA)

(73) Assignee: Panion & BF Biotech Inc. (TW)

( * ) Notice: Subject to any disclaimer, the term of this patent is extended or adjusted under 35 U.S.C. 154(b) by 0 days.

This patent is subject to a terminal disclaimer.

(21) Appl. No.: 14/502,774

(22) Filed: Sep. 30, 2014

(65) Prior Publication Data

US 2015/0232495 A1   Aug. 20, 2015

Related U.S. Application Data

(63) Continuation of application No. 14/011,357, filed on Aug. 27, 2013, now Pat. No. 8,846,976, which is a continuation of application No. 13/672,900, filed on Nov. 9, 2012, now Pat. No. 8,609,896, which is a continuation of application No. 12/711,679, filed on Feb. 24, 2010, now Pat. No. 8,338,642, which is a continuation of application No. 11/206,981, filed on Aug. 18, 2005, now Pat. No. 7,767,851, which is a continuation-in-part of application No. PCT/US2004/004646, filed on Feb. 18, 2004.

(60) Provisional application No. 60/462,684, filed on Apr. 15, 2003, provisional application No. 60/447,690, filed on Feb. 19, 2003.

(51) Int. Cl.
*C07C 51/41* (2006.01)
*C07F 15/02* (2006.01)
*A61K 31/295* (2006.01)

(52) U.S. Cl.
CPC .................................. *C07F 15/025* (2013.01)

(58) Field of Classification Search
None
See application file for complete search history.

(56) References Cited

U.S. PATENT DOCUMENTS

| | | | |
|---|---|---|---|
| 3,591,616 A | 7/1971 | Baldt | |
| 4,180,567 A | 12/1979 | Herb | |
| 4,689,322 A | 8/1987 | Kulbe et al. | |
| 4,970,079 A | 11/1990 | Hem et al. | |
| 5,206,265 A | 4/1993 | Vidic et al. | |
| 5,707,980 A | 1/1998 | Knutson et al. | |
| 5,753,706 A | 5/1998 | Hsu | |
| 6,887,897 B2 | 5/2005 | Walsdorf et al. | |
| 6,903,235 B2 | 6/2005 | Hsiao et al. | |
| 7,767,851 B2 * | 8/2010 | Kwok et al. | 562/590 |
| 8,338,642 B2 * | 12/2012 | Kwok et al. | 562/590 |
| 8,609,896 B2 * | 12/2013 | Kwok et al. | 562/590 |
| 8,754,257 B2 | 6/2014 | Chan et al. | |
| 8,754,258 B2 | 6/2014 | Kwok et al. | |
| 8,846,976 B2 * | 9/2014 | Kwok et al. | 562/590 |
| 8,901,349 B2 | 12/2014 | Kwok et al. | |
| 2005/0080283 A1 | 4/2005 | Hsia et al. | |
| 2006/0020026 A1 | 1/2006 | Kwok et al. | |
| 2008/0274210 A1 | 11/2008 | Chan et al. | |
| 2009/0186939 A1 | 7/2009 | Chan et al. | |

FOREIGN PATENT DOCUMENTS

| | | |
|---|---|---|
| AU | 199854419 | 7/1998 |
| AU | 723091 | 11/2000 |
| AU | 2004213819 | 8/2005 |
| AU | 2006279333 | 3/2008 |
| AU | 2007210090 | 7/2008 |
| AU | 2007210096 | 7/2008 |
| AU | 2004213819 | 12/2009 |
| CA | 2272711 | 5/1999 |
| CA | 2516471 | 8/2005 |
| CA | 2619591 | 2/2008 |
| CA | 2272711 | 4/2008 |
| CA | 2640763 | 7/2008 |
| CA | 2640974 | 7/2008 |
| CN | 1315174 | 10/2001 |
| CN | 1446790 | 10/2003 |
| CN | 1600302 | 3/2005 |
| CN | 03157490.4 | 3/2005 |
| CN | 1751056 A | 3/2006 |
| CN | 101019848 A | 8/2007 |
| CN | ZL 200480004726.7 | 5/2008 |
| CN | 101235186 A | 8/2008 |
| CN | 101374416 A | 2/2009 |
| CN | 101378658 A | 3/2009 |
| DE | 1131360 | 6/1962 |
| EA | 200501322/26 | 9/2005 |
| EA | 200800593/26 | 3/2008 |
| EA | 010028 | 6/2008 |
| EP | 0308362 | 3/1989 |
| EP | 0600347 | 6/1994 |
| EP | 0959878 | 12/1999 |

(Continued)

OTHER PUBLICATIONS

U.S. Appl. No. 60/447,690, filed Feb. 19, 2003, Kwok et al.

(Continued)

*Primary Examiner* — Yevegeny Valenrod

(74) *Attorney, Agent, or Firm* — Law Offices of Albert Wai-Kit Chan, PLLC

(57) ABSTRACT

The present invention discloses a novel form of ferric organic compounds, including a form of ferric citrate, which are soluble over a wider range of pH, and which have a large active surface area. The ferric organic compounds of the present invention can be delivered effectively by oral route with better delivery to treat patients suffering from hyperphosphatemia, metabolic acidosis and other disorders responsive to ferric organic compound therapy.

18 Claims, 5 Drawing Sheets

(56) References Cited

FOREIGN PATENT DOCUMENTS

| | | |
|---|---|---|
| EP | 1601680 | 12/2005 |
| EP | 1931689 | 6/2008 |
| EP | 0959878 | 7/2008 |
| EP | 1978807 | 10/2008 |
| EP | 1978808 | 10/2008 |
| GB | 1224589 | 3/1971 |
| GB | 1226394 | 3/1971 |
| GB | 2212396 A | 7/1989 |
| HK | 1077580 A | 2/2006 |
| ID | W00200502228 | 8/2005 |
| IL | 170382 | 8/2005 |
| IL | 130041 | 12/2005 |
| IL | 189583 | 2/2008 |
| IL | 193099 | 7/2008 |
| IL | 192545 | 8/2008 |
| IN | 00944/MUMNP/2005 | 8/2005 |
| IN | 393/MUMNP/2008 A | 3/2008 |
| IN | 1414/MUMNP/2008 | 7/2008 |
| IN | 14143/MUMNP/2008 | 7/2008 |
| IN | 244119 | 11/2010 |
| JP | 8198760 A | 8/1996 |
| JP | 2007-133978 | 11/1997 |
| JP | 2001-506262 | 5/2001 |
| JP | 2006-518391 | 8/2006 |
| JP | 2008-552431 | 7/2008 |
| JP | 2008-552435 | 7/2008 |
| JP | 4173553 | 8/2008 |
| JP | 2009-24341 | 2/2009 |
| JP | 2009-504777 | 2/2009 |
| KR | 10-2000-0069414 | 11/2000 |
| KR | 464504 | 12/2004 |
| KR | 10-2005-0107428 | 11/2005 |
| KR | 10-2008-70106131 | 4/2008 |
| KR | 10-2008-0094013 | 10/2008 |
| KR | 10-2008-0106506 | 12/2008 |
| LK | 13792 | 8/2005 |
| MX | 207250 | 3/2002 |
| MX | PA05008784 A | 5/2006 |
| MX | MX/A/2008/002360 | 2/2008 |
| MX | MX/A/2011/000585 | 1/2011 |
| MY | PI 2006-3971 | 8/2006 |
| NO | 19992936 | 6/1999 |
| NO | 327148 | 5/2009 |
| NZ | 336060 | 6/1999 |
| NZ | 541991 | 2/2004 |
| NZ | 566743 | 3/2008 |
| NZ | 541991 | 2/2009 |
| NZ | 566743 | 11/2010 |
| PG | PG/P/05/00029 | 8/2005 |
| PH | 1-2005-501521 | 8/2005 |
| RU | 2188033 | 8/2002 |
| SG | 200505259-2 | 8/2005 |
| SG | 114272 | 8/2007 |
| SU | 142643 | 3/1961 |
| TL | 061003938 | 8/2006 |
| TW | 86104116 | 3/1997 |
| TW | 93103743 | 2/2004 |
| TW | 259772 B | 8/2006 |
| TW | 95130373 | 8/2006 |
| VN | 1-2005-01292 | 9/2005 |
| VN | 8033 | 11/2009 |
| WO | WO/98/26776 | 6/1998 |
| WO | WO/2004/074444 | 9/2004 |
| WO | WO/2007/022435 | 2/2007 |
| WO | WO/2007/089571 | 8/2007 |
| WO | WO/2007/089577 | 8/2007 |

OTHER PUBLICATIONS

U.S. Appl. No. 60/462,684, filed Apr. 15, 2003, Kwok et al.
U.S. Appl. No. 60/709,511, filed Aug. 19, 2005, Kwok et al.
U.S. Appl. No. 12/064,058, filed Feb. 18, 2008, Chan et al.
U.S. Appl. No. 12/162,558, filed Jul. 29, 2008, Chan et al.
U.S. Appl. No. 12/162,543, filed Oct. 29, 2008, Chan et al.
PCT International Search Report, Feb. 10, 1998, for Hsu, Chen Hsing, International App'l No. PCT/US1997/020977, filed Nov. 14, 1997.
PCT Written Opinion of the International Searching Authority, Nov. 12, 1998, for Hsu, Chen Hsing, International App'l No. PCT/US1997/020977 filed Nov. 14, 1997.
PCT International Preliminary Examination Report, Mar. 2, 1999, for Hsu, Chen Hsing, International App'l No. PCT/US1997/020977, filed Nov. 14.
PCT International Search Report, Jan. 26, 2005, for GloboAsia, LLC, et al., International Application No. PCT/US2004/004646, filed Feb. 18, 2004.
PCT Written Opinion of the International Searching Authority, Jan. 26, 2005, for GloboAsia, LLC, et al., Int'l Application No. PCT/US2004/004646, filed Feb. 18, 2004.
PCT International Preliminary Report on Patentability, Aug. 19, 2005, for GloboAsia, LLC, et al., International Application No. PCT/US2004/004646, filed Feb. 18, 2004.
PCT International Search Report, Nov. 26, 2007, for GloboAsia, LLC, et al., International Application No. PCT/US2007/002151, filed Jan. 26, 2007.
PCT Written Opinion of the International Searching Authority, Nov. 26, 2007, for GloboAsia, LLC, et al., Int'l Application No. PCT/US2007/002151, filed Jan. 26, 2007.
PCT Written Opinion of the International Searching Authority, Mar. 2, 2007, GloboAsia, LLC, et al., International Application No. PCT/US2006/032385, filed Aug. 18, 2006.
PCT International Search Report, Mar. 2, 2007, GloboAsia, LLC, et al., International Application No. PCT/US2006/032385, filed Aug. 18, 2006.
PCT International Search Report, Dec. 5, 2007, for GloboAsia, LLC, et al., International Application No. PCT/US2007/002157, filed Jan. 26, 2007.
PCT Written Opinion of the International Searching Authority, Dec. 5, 2007, for GloboAsia, LLC, et al., Int'l Application No. PCT/US2007/002157, filed Jan. 26, 2007.
PCT International Preliminary Report on Patentability, Feb. 28, 2008, for GloboAsia, LLC, et al., International Application No. PCT/US2006/032385, filed Aug. 18, 2006.
Austrian Written Opinion, Jul. 7, 2006, for GloboAsia, LLC, Singapore Application No. 200505259-2, filed Aug. 18, 2005.
Austrian Examination Report issued Mar. 16, 2007, for GloboAsia, LLC, Singapore Application No. 200505259-2, filed Aug. 18, 2005.
Australian Examiner's First Report, May 8, 2009, for Australian Application No. 2004213819, filed Aug. 23, 2005.
Australian Notice of Acceptance, Aug. 18, 2009, for Australian Application No. 2004213819, filed Aug. 23, 2005.
Canadian Office Action, Jan. 18, 2005, for Chen Hsing Hsu, Canadian Application No. 2,272,711, Filed May 26, 1999.
Canadian Office Action, Dec. 22, 2005, for Chen Hsing Hsu, Canadian Application No. 2,272,711, Filed May 26, 1999.
Canadian Office Action issued Sep. 15, 2006 for Chen Hsing Hsu, Canadian Application No. 2,272,711, filed May 26, 1999.
Canadian Notice of Allowance, Aug. 10, 2007, for Chen Hsing Hsu, Canadian Application No. 2,272,711, filed May 26, 1999.
Canadian Office Action, Aug. 30, 2010, for Canadian Application No. 2,516,471, Filed Aug. 18, 2005.
Chinese Pre-Exam Results, Nov. 21, 2003, for Hsiao et al., Chinese Application No. 03157490.4, filed Sep. 22, 2003. (w/English Translation).
Chinese Office Action, Aug. 12, 2005, for Hsiao et al., Chinese Application No. CN 03157490.4, filed Sep. 22, 2003. (w/English Translation).
Chinese Search Report issued Nov. 3, 2006 for GloboAsia, LLC, Chinese Application Publication No. CN 200480004726.7, filed Aug. 19, 2005.
Chinese Office Action, Aug. 17, 2007, for GloboAsia, LLC, Chinese Publication No. CN 200480004726.7, filed Aug. 19, 2005.
Chinese Notification for the Grant of Invention Patent Rights, Nov. 16, 2007, for GloboAsia, LLC, Chinese App. Publication No. CN 1751056A, filed Mar. 22, 2006.
Chinese Notification for Completion of Formalities for Registration, Dec. 5, 2007, for GloboAsia, LLC, Chinese App. Publication No. CN 1751056A, filed Mar. 22, 2006.

(56) References Cited

OTHER PUBLICATIONS

Eurasian Search Report issued Mar. 26, 2007, for GloboAsia, LLC, Eurasian Application No. 200501322/28, filed Sep. 19, 2005.
Eurasian Notification of Readiness to Grant a Eurasian Patent, Oct. 26, 2007, for GloboAsia, LLC, Eurasian Application No. 200501322/28, filed Sep. 19, 2005.
Eurasian Notification on the Necessity of Presenting Additional Materials, Jul. 3, 2009, for Eurasian App. No. 200800593/28, filed Mar. 18, 2008.
Supplementary Partial European Search Report, Jan. 28, 2002, for Chen Hsing Hsu, European Application No. 97948333.6, Filed Nov. 14, 1997.
European Office Communication, Jun. 16, 2003, for Chen Hsing Hsu, European Application No. 97948333.6, filed Nov. 14, 1997.
European Office Communication, May 16, 2006, for Chen Hsing Hsu, European Application No. 97948333.6, filed Nov. 14, 1997.
European Communication under Rule 71(3) EPC, Jan. 21, 2008, for Chen Hsing Hsu, European Application No. 97948333.6, Filed Nov. 14, 1997.
Eurasian Decision to Grant a Eurasian Patent, Mar. 6, 2008, for GloboAsia, LLC, Eurasian Application No. 200501322, Filed Feb. 18, 2004.
Supplementary European Search Report, Apr. 28, 2008, for GloboAsia, et al., European Application No. EP 04712312.0, Filed Sep. 19, 2005.
European Decision to Grant a European Patent Pursuant to Article 97(1) EPC, Jun. 12, 2008, Hsu, Chen Hsing, European App. No. 97948333.6, filed Nov. 14, 1997.
European Office Communication, Feb. 18, 2009, for GloboAsia, LLC, et al., European Application No. EP 04712312.0, filed Sep. 19, 2005.
European Office Communication, Aug. 4, 2009, for European Application No. 04712312.0, filed Sep. 13, 2005.
U.S. Final Office Action, Jun. 24, 2014, for Kwok et al., U.S. Appl. No. 14/011,325, filed Aug. 27, 2013.
Japanese Office Action of Notice of Reasons for Rejection, Jun. 17, 2014, for Yusuke Hiraki & Ors., Japanese Application No. JP 2013-103220, Filed May 15, 2013. [Exhibit 1].
Israeli Office Action, Sep. 15, 2014, for Panion & BF Biotech, Inc., Israeli Patent Application No. 228952, Filed Oct. 22, 2013. [Exhibit 2].
Indian First Examination Report, Mar. 12, 2009, for Indian Application No. 944/MUMNP/2005, filed Aug. 24, 2005.
Israeli Office Action, Nov. 16, 2000, for Chen-Hsing Hsu, Israeli Application No. 130041, Filed May 19, 1999.
Israeli Office Action, Apr. 16, 2008, for GloboAsia, LLC et al., Israeli Application No. 170382, Filed Aug. 18, 2005.
Israeli Office Action, Feb. 8, 2009, for GloboAsia, LLC, et al., Israeli Application No. 170382, filed Aug. 18, 2005.
Israeli Office Action, Aug. 17, 2009, for Israeli Application No. IL 170382, filed Aug. 18, 2005.
Israeli Preliminary Office Action, Sep. 3, 2009, for Israeli Application No. IL 189583, filed Aug. 18, 2006.
Israeli Preliminary Office Action, Nov. 15, 2009, for Israeli Application No. IL 192545, filed Jun. 30, 2008.
Israeli Preliminary Office Action, Dec. 3, 2009, for Israeli Application No. IL 193099, filed Jul. 28, 2008.
Japanese Office Action, Nov. 22, 2006, for Chen Hsing Hsu, Japanese Application No. 10-527705, filed Jun. 15, 1999 (w/English translation).
Japanese Office Action, Aug. 29, 2007, for Chen Hsing Hsu, Japanese Application No. 10-527705, filed Jun. 15, 1999.
Japanese Decision to Grant, Jul. 16, 2008, for Hsu, Chen Hsing, Japanese Application No. JP 10-527705, filed Jun. 15, 1999.
Japanese Office Action, Mar. 16, 2010, for GloboAsia, LLC, Japanese Application No. 2006-503637, Filed Aug. 18, 2005.
Korean Office Action, Jun. 22, 2004, for Chen Hsing Hsu, Korean Application No. 10-1999-7005186, Filed Jun. 10, 1999.
Korean Notice of Decision for Patent, Oct. 26, 2004, for Chen Hsing Hsu, Korean Application No. 10-1999-7005186, Filed Jun. 10, 1999.
Malaysian Substantive Examination Adverse Report, Mar. 27, 2009, for Malaysian App'l No. PI 20063971, filed Aug. 18, 2006.
Mexican Examination Report, Aug. 5, 2009, for Mexican Application No. PA/a/2005/008784, filed Aug. 18, 2005.
Mexican Office Action, Feb. 23, 2010, for GloboAsia, LLC, Mexican Application No. PA/A/2005/008784, Filed Aug. 18, 2005.
Mexico Office Action, Sep. 7, 2010, for Mexican Application No. PA/a/2005/008784, filed Aug. 18, 2005.
New Zealand Examiner's Report, Jul. 16, 1999, for Chen Hsing Hsu, New Zealand Application No. 336060, filed Jun. 1, 1999.
New Zealand Examiner's Report, Jul. 25, 2007, for GloboAsia, LLC, New Zealand Application No. 541991, filed Sep. 19, 2005.
New Zealand Examination Report, May 15, 2008, for GloboAsia, LLC et al., New Zealand Application No. NZ 541991, filed Feb. 18, 2007.
New Zealand Office Action, Mar. 29, 2010, for GloboAsia, LLC, New Zealand Application No. 566743, Filed Mar. 17, 2008.
Norwegian Office Action issued Jan. 15, 2007, for Chen Hsing Hsu, Norwegian Application No. 19992936, filed Jun. 16 1999.
Norwegian Office Action, Oct. 17, 2007, for Chen Hsing Hsu, Norwegian Application No. 19992936, filed Jun. 16, 1999.
Norwegian Office Action, Apr. 17, 2008, for Hsu, Chen Hsing, Norwegian Application No. NO 19992936, filed Jun. 16, 1999.
Papua New Guinea Search and Examination Report, May 5, 2009, for Papua New Guinea Application No. PG/P/2005/00029, filed Aug. 22, 2005.
Philippine Examination Report, Dec. 16, 2008, for Philippine Application No. 1-2005-501521, filed Aug. 19, 2005.
Taiwan Office Action, Apr. 13, 1999, for Chen Hsing Hsu, Taiwanese Application No. 86104116, filed Mar. 31, 1997. (w/English Translation).
Taiwan Patent Re-Examination Appeal Notice, Aug. 10, 1999, for Chen Hsing Hsu, Taiwanese App. No. 86104116, filed Mar. 31, 1997. (w/English Trans).
Taiwan Office Action, Aug. 30, 1999, for Chen Hsing Hsu, Taiwanese Application No. 86104116, filed Mar. 31, 1997. (w/English Translation).
Taiwan Notice of Allowance, Jun. 16, 2006, for Hsiao et al., Taiwan Application No. TW 092124445, filed Sep. 4, 2003.
Taiwan Office Action, Aug. 1, 2006, for Kwok et al., Taiwan Application No. TW 093103743, filed Feb. 17, 2004.
Taiwan Office Action, Feb. 1, 2007, for Kwok et al., Taiwan Application No. TW 093103743, filed Feb. 17, 2004.
Taiwan Office Action, Mar. 18, 2007, for Kwok et al., Taiwan Application No. TW 093103743, filed Feb. 17, 2004.
Thailand Office Action, Nov. 15, 2007, for GloboAsia, LLC, Thailand Application No. 0601003938, filed Aug. 17, 2006.
U.S. Office Action, Jul. 7, 1997, for Chen Hsing Hsu, U.S. Appl. No. 08/794,328, filed Feb. 3, 1997.
U.S. Notice of Allowance and Fee(s) Due, Jan. 7, 1998, for Chen Hsing Hsu, U.S. Appl. No. 08/794,328, filed Feb. 3, 1997.
U.S. Office Action, Jun. 1, 2004, for Hsiao, et al., U.S. Appl. No. 10/682,045, filed Oct. 8, 2003.
U.S. Office Action, Sep. 22, 2004, for Hsiao, et al., U.S. Appl. No. 10/682,045, filed Oct. 8, 2003.
U.S. Notice of Allowance and Fee(s) Due, Jan. 26, 2005, for Hsiao, et al., U.S. Appl. No. 10/682,045, filed Oct. 8, 2003.
U.S. Office Action, Mar. 5, 2007, for U.S. Appl. No. 11/206,981, filed Aug. 18, 2005.
U.S. Office Action, Sep. 24, 2007, for U.S. Appl. No. 11/206,981, filed Aug. 18, 2005.
U.S. Office Action, Dec. 6, 2007, for U.S. Appl. No. 11/206,981, filed Aug. 18, 2005.
U.S. Office Action, Jun. 13, 2008, for U.S. Appl. No. 11/206,981, filed Aug. 18, 2005.
U.S. Office Action, Feb. 26, 2009, for U.S. Appl. No. 11/206,981, filed Aug. 18, 2005.
U.S. Notice of Allowance and Fees Due, Oct. 5, 2009, for U.S. Appl. No. 11/206,981.
U.S. Office Action, Jul. 27, 2010, for Chan et al., U.S. Appl. No. 12/162,543, "Method of Treating Chronic Kidney Disease", filed Jul. 29, 2008.

(56) References Cited

OTHER PUBLICATIONS

Vietnam Office Action, Jan. 9, 2008, for GloboAsia, LLC, Vietnam Application No. 1-2005-01292, filed Feb. 18, 2004.
Vietnam Notification, Apr. 28, 2009, for Kwok et al., Vietnam Application No. 1-2005-01292, filed Feb. 18, 2004.
Vietnam Notification on Result of Substantive Examination, Sep. 29, 2009, for Vietnam Application No. VN-1-2005-01292, filed Feb. 18, 2004.
Almaden, et al., 1995, "High Phosphorous Directly Stimulates PTH Secretion by Human Parathyroid Tissue", Journal of the American Society of Nephrology, vol. 6: 957.
American Chemical Society, Feb. 6, 1961, "Ferric Citrate", Chemical Abstracts, vol. 55 (3): 3939d.
Anjyo, et al., 1944, "Medication Advice for Patients with Hypoferric Anemia", Yakkyoku, vol. 45(5): 55-59. (w/English Abstract).
Barer et al., 1940, "The Effect of Iron on Phosphorous, Calcium, and Nitrogen Metabolism", Journal of Laboratory & Clinical Medicine, vol. 26: 351-360.
Block et al., 2000, "Re-Evaluation of Risks Associated with Hyperphosphatemia and Hyperparathyroidism . . . Management", American Journal of Kidney Diseases, vol. 35(6):1226-1237.
Brock, et al., 1934, "Rickets in Rats by Iron Feeding", Journal of Pediatrics, vol. 4:442-453.
Clarkson, et al., 1966, "The Effect of a High Intake of Calcium Carbonate in Normal Subjects and Patients with Chronic Renal Failure", Clinical Science, vol. 30: 425-438.
Coburn, et al., 1973, "Study of Intestinal Absorption of Calcium in Patients with Renal Failure", Kidney International, vol. 3: 264-272.
Coburn, et al., 1973, "Intestinal Absorption of Calcium and the Effect of Renal Insufficiency", Kidney International, vol. 4: 96-104.
Cox, et al., 1931, "The Effects of High Doses of Aluminum and Iron on Phosphorous Metabolism", Journal of Biological Chemistry, vol. 92: Xi-Xii.
Cullen, et al., 2008, "A 28-Day Toxicity Study of KRX-0502 (Ferric Citrate) in Rats by Dietary Administration, Keryx Biopharmaceuticals, Inc." (poster presentation).
Cullen, et al., 2008, "A 28-Day Toxicity Study of KRX-0502 (Ferric Citrate) in Rats by Dietary Administration, Keryx Biopharmaceuticals, Inc." (abstract only).
Deobald, et al., 1935, "The Effect of Feeding High Amounts of Soluble Iron and Aluminum Salts", American Journal of Physiology, vol. 111: 118-123.
Editorial [No Author], 1986, "Citrate for Calcium Nephrolithiasis," The Lancet, vol. 330, Issue 8487: 955.
Ghosh, Amit Kumar, 2002, "Letters and Replies: Efficacy of Ferric Citrate . . . in End-stage Renal Failure", Nephrology Dialysis Transplantation, vol. 17:1354-1355.
Gimenez, et al., 1982, "Prevention of Phosphate-induced Progression of Uremia in Rats by 3-phosphocitric Acid", Kidney International, vol. 22: 36-41.
Goodman et a., 2000, "Coronary-Artery Calcification in Young Adults with End-Stage Renal . . . Undergoing Dialysis", The New England Journal of Medicine, vol. 342:1478-1483.
Gutteridge J.M.C., 1991, "Hydroxyl Radical Formation from the Auto-Reduction of a Ferric Citrate Complex", Free Radical Biology and Medicine, vol. 11(4):401-406.
Haut, et al., 1980, "Renal Toxicity of Phosphate in Rats", Kidney International, vol. 17: 722-731.
Hollis, Bruce W., 1986, "Assay of Circulating 1,25-Dihydroxyvitamin D . . . Extraction and Purification Procedure", Clinical Chemistry, vol. 32:2060-2063.
Hou, et al., 1991, "Calcium and Phosphorous Fluxes During Hemodialysis with Low Calcium Dialysate", American Journal of Kidney Diseases, vol. 18: 217-224.
Hsu, Chen Hsing, Apr. 1997, "Are We Mismanaging Calcium and Phosphate Metabolism in Renal Failures?", American Journal of Kidney Diseases, vol. 29(4): 641-69.
Hsu, et al., 1984, "Renal Phosphate Excretion in Spontaneously Hypertensive and Normotensive Wistar Kyoto rats", Kidney International, vol. 25: 789-795.

Hsu, et al., 1990, "Factors Influencing Calcitriol Metabolism in Renal Failure", Kidney International, vol. 37: 44-50.
Hsu, et al., 1999, "New Phosphate Binding Agents: Ferric Compounds", Journal of the American Society of Nephrology, vol. 10:1274-1280.
in-Pharma Technologist.com, Jun. 8, 2005, "Pharma-grade ferric citrate patented", Sep. 17, 2008, http://www.in-pharmatechnologist.com/Materials-Formulation/Pharma . . . .
Jacobs, A. & P. M. Miles, 1969, "Role of gastric secretion in iron absorption," Gut 10:226-229.
Japan, 1999, "Japan's Specifications and Standard for Food Additives", vol. 7: D205-208, D376-382, D428-430, D552-554, D936-938, D1030-1032, D1425-1428.
Karlinsky, et al., 1980, "Preservation of Renal Function in Experimental Glomerulonephritis", Kidney International, vol. 17: 293-302.
Kawatetsu Techno Res. KK, 2003, "Manufacture of Ferric Ammonia citrate, for Supplying Iron Ions in Chemical Reaction . . . Iron Citrate", WPIDS (abstract only).
Kilav, et al., 1995, "Parathyroid Hormone Gene Expression in Hypophosphatemic Rats", Journal of Clinical Investigation, vol. 96: 327-333.
King, Earl Judson, 1939, "The Biochemistry of Silicic Acid: The Determination of Silica", The Biochemical Journal, vol. 33(6):944-954.
King, et al., 1938, "The Biochemistry of Silicic Acid: The Solution and Excretion of Silica", The Biochemical Journal, vol. 32(2):426-433.
Kuroda, et al., 1995, "Effect of Iron as a New Type of Phosphate Binder in Hemodialysis Patients", Japan J Nephrol, vol. 37, 468-473.
Lakshmanan, et al., 1984, "Calcium and Phosphorus Intakes, Balances, and Blood Levels . . . Self-selected Diets", American Journal of Clinical Nutrition vol. 40:1368-1379.
Lau, Kai, 1989, "Phosphate Excess and Progressive Renal Failure: The Precipitation-Calcification Hypothesis", Kidney International, vol. 36: 918-937.
Lau, et al., 1990, "Fluids and Electrolytes", W.B. Saunders Company, Second Edition, Philadelphia, Ch. 8: 505-595.
Liu, et al., 1943, "Studies of Calcium and Phosphorous Metabolism . . . Dihydrotachysterol (A.T.10) and Iron", Medicine, vol. 22:103-161.
Lopez-Hilker, et al., 1990, "Phosphorous Restriction Reverses Hyperparathyroidism in Uremia . . . Calcitriol", American Journal of Physiology, vol. 259:F432-437.
Lumlertgul, et al., 1986, "Phosphate Depletion Arrests Progression of Chronic Renal Failure Independent of Protein Intake", Kidney International, vol. 29: 658-666.
Martis, et al., 1989, "Calcium Cabonate as a Phosphate Binder: Is There a Need to Adjust . . . for Patients Using CaCO3?", Peritoneal Dialysis International, vol. 9:325-328.
Matkovic, et al., 1992, "Calcium Balance during Human Growth: Evidence for Threshold Behavior", American Journal of Clinical Nutrition, vol. 55: 992-996.
Meyer, et al., 1982, "Trace Metal-Citric Acid Complexes as Inhibitors of Calcification and . . . Phosphate Crystal Growth", J Urol, vol. 128, No. 6, 1372-1375.
Moore, C.V., 1968, Entry for "Iron", in Modern Nutrition in Health and Disease, Michael G. Wohl and Robert S. Goodhart Eds., Published by Lea & Febiger, Philadelphia;p. 339-364.
Naveh-Many, et al., 1995, "Parathyroid Cell Mitoses in Normal and Chronic Renal Failure Rats: . . . Vitamin D", American Society of Nephrology, vol. 6: 968.
Niecestro et al., 2006, A Phase II, Randomized, Double-Blind, Placebo-Controlled, Dose-Ranging Study of Ferric Citrate (FC) on Serum Phosphorous Levels in ESRD Patients. Abs.
Niecestro, Robert, 2006, "Ferric Citrate for the Treatment of Hyperphosphatemia in ESRD" Abstract of article to be filed.
Niecestro, et al., 2007, "A Randomized, Double-Blind, Placebo-Controlled Dose Ranging Study of the Effects . . . Renal Disease (ESRD)", Article to be published.
Niecestro, Robert, Apr. 21, 2007, "Ferric Citrate for the Treatment of Hyperphosphatemia in ESRD", 2007 World Congress of Nephrology Conference, pp. 160-161.

(56) References Cited

OTHER PUBLICATIONS

Niecestro et al., 2006, "Ferric Citrate (Phosphate Binder): Effects on Serum Iron and Other Parameters in ESRD Patients." (Abstract only).
Niecestro et al., 2006, "A Randomized, Double-Blind, Placebo-Controlled, Dose-Ranging Study . . . (ESRD)." (PowerPoint Presentation made at Renal Week of the American Society.
Piraino, et al., 1992, "Calcium Mass Transfer in Peritoneal Dialysis Patients Using 2.5 mEg/l Calcium Dialysate", Clinical Nephrology, vol. 37: 48-51.
Portale, et al., 1989, "Effect of Dietary Phosphorous on Circulating . . . Renal Insufficiency", Journal of Clinical Investigation, vol. 73: 1580-1589.
Princiotto et al., 1970, "Absorption of Oral Chelated Iron", Biochemical Medicine, vol. 3: 289-297.
Ramirez, et al., 1986, "The Absorption of Dietary Phosphorus and Calcium in Hemodialysis Patients", Kidney International, vol. 30: 753-759.
Rehm, et al., 1940, "The Effect of Ferric Chloride on the Utilization of Calcium and Phosphorous in the Animal Body", Journal of Nutrition, vol. 19: 213-222.
Reinhardt, et al., 1984, "A Microassay for 1,25-Dihydroxyvitamin D . . . Clinical Studies", Journal of Clinical Endocrinology and Metabolism, vol. 58(1): 91-98.
Rivet et al., 2006, "Cutaneous Calcification in Patients with End-Stage Renal Disease," Arch. Dermatol., vol. 142: 900-906.
Sika et al., 2009, "Evaluation of Ferric Citrate as . . . Phosphate Binder", Zerenex Poster presented at the American Society of Nephrology Conference, Oct. 2009.
Slaptopolsky, et al., 1971, "On the Pathogenesis of Hyperparathyroidism in Chronic . . . Dog", Journal of Clinical Investigations, vol. 50: 492-499.
Slaptopolsky, et al., 1995, "Phosphate (PO) Restriction Prevents Parathyroid Cell Growth in Uremic Rats . . . Tissue Culture", American Society of Nephrology, vol. 6: 971.
Spiro, et al., 1967, "The Hydrolytic Polymerization of Ferric Citrate. T. The Chemistry of the Polymer", Journal of the American Chemical Society, vol. 89: 5555-5559.
Terato, et al., 1972, "Studies on Intestinal Absorption of Iron . . . Polymerization of Iron", Journal of the Pharmaceutical Society of Japan, vol. 92(10):1247-1251.
The Ferric Citrate Study Group, 2007, "A Phase II Ramdomized, Double-Blind, Placebo-Controlled, Dose-Ranging Study of Ferric Citrate (FC) on Serum Phosphorous Levels" Abs.
The Ferric Citrate Study Group, 2007, "Ferric Citrate: Effects on Iron Parameters, Hematocrit, and Hemoglobin in End-Stage Renal Disease Patients" Abs.
The Ferric Citrate Study Group, 2006, "A Phase II Ramdomized, Double-Blind, Placebo-Controlled, Dose-Ranging Study of Ferric Citrate (FC) on Serum Phosphorous Levels" Abs.
The Ferric Citrate Study Group, 2006, "Effects on Iron Parameters in End-Stage Renal Disease Patients" Abstract of Patent application to be filed.
The Merck Index, 1996, 12th Ed., "Acetic, Citric, Fumaric, Isocitric, succinic, and tartaric acid".
Thomas, W.C., 1982, "Trace Metal-Citric Acid Complexes as Inhibitors of Calcification and Crystal Formation", Proc. Soc. Exp. Biol. Med., vol. 170, No. 3, 321-327.
Webster's II New Riverside University Dictionary, 1984, Riverside Publishing Company, p. 763.
Yamamoto, et al., 1995, "Interaction between Various Phosphate Compounds and Iron Compounds Containing Sodium Ferrous Citrate", Shinyaku & Rinsho, vol. 44(5):9-15. (w/Eng.Abs.
Yang, et al., 2002, "An Open-Label, Crossover Study of a New Phosphate-Binding Agent in Haemodialysis Patients: Ferric Citrate",Nephr. Dialysis Transplantation, vol. 17:265-270.
European Office Action, Nov. 10, 2010, for GloboAsia LLC, European Application No. 04712312.0, Filed Sep. 13, 2005.
Israeli Office Action, Sep. 14, 2010, for GloboAsia LLC, Israeli Application No. IL 193099, filed Jul. 28, 2008.
Israeli Office Action, Sep. 5, 2010, for GloboAsia LLC, Israeli Application No. IL 192545, filed Jun. 30, 2008.
Japanese Office Action, Dec. 16, 2010, for Chen Hsing Hsu, Japanese Application No. JP 2007-133978, filed May 21, 2007.
Mexico Office Action, Oct. 4, 2010, for GloboAsia LLC, Mexican Application No. MX/A/2008/002360, filed Aug. 18, 2005.
European Extended Search Report, Jan. 12, 2011, for GloboAsia LLC, European Application No. 06813544.1, filed Mar. 18, 2008.
Chinese Office Action, Jan. 27, 2011, for GloboAsia LLC, Chinese Application No. 200680032108.2, filed Feb. 29, 2008.
U.S. Office Action, Oct. 22, 2010, for Chan et al., U.S. Appl. No. 12/064,058, filed Feb. 18, 2008.
U.S. Office Action, Nov. 24, 2010, for Chan et al., U.S. Appl. No. 12/162,543, filed Jul. 29, 2008.
U.S. Office Action, Jan. 12, 2011, for Chan et al., U.S. Appl. No. 12/162,558, filed Jul. 29, 2008.
Australian Examination Report, Jun. 20, 2011, for GloboAsia LLC, Australian Application No. 2006279333, Filed Mar. 14, 2008.
Australian Examination Report, Dec. 20, 2011, for GloboAsia LLC, Australian Application No. 2006279333, Filed Mar. 14, 2008.
Australian Examination Report, Mar. 28, 2012, for GloboAsia LLC, Australian Application No. 2006279333, Filed Mar. 14, 2008.
Canadian Office Action, May 10, 2011, for GloboAsia, LLC, Canadian Applicaiton No. 2,516,471, Filed Aug. 18, 2005.
Canadian Office Action, Jan. 31, 2012, for GloboAsia LLC, Canadian Patent No. 2,516,471, Filed Aug. 18, 2005.
Chinese First Office Action, Jun. 9, 2011, for GloboAsia LLC, Chinese Application No. 200780003990.2, Filed Jun. 29, 2008.
Chinese Office Action, Dec. 7, 2011, for GloboAsia LLC, Chinese Application No. 200780003983.2, Filed Jul. 30, 2008.
Chinese Office Action, Dec. 31, 2011, for GloboAsia LLC, Chinese Application No. 200680032108.2, Filed Feb. 29, 2008.
Chinese Office Action, Apr. 13, 2012, for GloboAsia LLC, Chinese Application No. 200780003990.2, Filed Jul. 30, 2008.
Chinese Rejection Decision, May 3, 2012, for GloboAsia LLC, Chinese Application No. 200680032108.2, Filed Feb. 29, 2008.
Eurasian Office Action, Jun. 27, 2011, for GloboAsia LLC, Eaurasian Application No. 200800593, Filed Mar. 18, 2008.
Eurasian Office Action, Mar. 22, 2012 for Eurasian Application No. 200800593, Filed Mar. 8, 2008.
European Search Report, Mar. 12, 2012, for GloboAsia LLC, European Applicaiton No. EP11155958.9, Filed Feb. 25, 2011.
European Search Report, Apr. 16, 2012, for GloboAsia LLC, European Application No. EP07762833.7, Filed Jun. 29, 2008.
European Search Report, Apr. 18, 2012, for GloboAsia LLC, European Application No. EP07717051.2, Filed Jun. 29, 2008.
Indian Examination Report, Jan. 17, 2012, for GloboAsia LLC, Indian Application No. 1413/MUMNP/2008, Filed Jul. 7, 2008.
Indian Examination Report, Jan. 23, 2012, for GloboAsia LLC, Indian Application No. 1414/MUMNP/2008, Filed Jul. 7, 2008.
Israeli Office Action, Jul. 10, 2011, for GloboAsia LLC, Israeli Application No. 189583, Filed Feb. 18, 2008.
Israeli Office Action, Dec. 19, 2011, for GloboAsia LLC, Israeli Applciation No. 189583, Filed Feb. 18, 2008
Japanese Final Rejection, May 24, 2011, for GloboAsia LLC, Japanese Application No. JP 2006-503637, Filed Aug. 18, 2005.
Japanese Final Office Action, Nov. 15, 2011, for GloboAsia LLC, Japanese Application No. 2006-503637, Filed Aug. 18, 2005.
Japanese Office Action, Mar. 13, 2012, for GloboAsia LLC, Japanese Application No. 2008-527177, Filed Feb. 18, 2008.
Korean Final Office Action, Sep. 29, 2011, for GloboAsia LLC, Korean Application No. 10-2005-7014976, Filed Aug. 12, 2005.
Korean Office Action, Feb. 7, 2011, for GloboAsia LLC, Korean Application No. 10-2005-7014976, Filed Aug. 12, 2005.
Mexican Office Action, May 27, 2011, for GloboAsia LLC, Mexican Application No. MX/A/2008/002360, Filed Feb. 18, 2008.
Mexican Office Action, Mar. 29, 2011, for GloboAsia LLC, Mexican Application No. PA/A/2005/008784, Filed Aug. 18, 2005.
Philipine Office Action, Jul. 20, 2011, for GloboAsia LLC, Philippines App'l No. 1-2005-501521, Filed Aug. 19, 2005.
Taiwanese Office Action, Jul. 27, 2010, for GloboAsia LLC, Taiwanese Application No. 093103743, Filed Feb. 17, 2004.

(56) References Cited

OTHER PUBLICATIONS

Taiwanese Office Action, May 1, 2012, for GloboAsia LLC, Taiwanese Application No. 95130373, Filed Aug. 18, 2006.
U.S. Office Action, Jun. 7, 2011, for GloboAsia, LLC for U.S. Appl. No. 12/162, 558, filed Jul. 29, 2008.
U.S. Final Office Action, Jan. 4, 2012, for GloboAsia LLC, U.S. Appl. No. 12/162,543, filed Jul. 29, 2008.
U.S. Office Action, May 8, 2012, for GloboAsia LLC, U.S. Appl. No. 13/289,048, filed Nov. 4, 2011.
U.S. Office Action, Mar. 8, 2011, for GloboAsia LLC, U.S. Appl. No. 12/064,058, filed Feb. 18, 2008.
U.S. Final Office Action, Aug. 5, 2011, for GloboAsia LLC, U.S. Appl. No. 12/162,543, filed Jul. 29, 2008
U.S. Final Office Action, Dec. 7, 2011, for GloboAsia LLC, U.S. Appl. No. 12/162,558, filed Jul. 29, 2008.
PCT International Search Report, Nov. 25, 2010, for Henry Trong Le, International App'l No. PCT/US2010/042788, Filed Jul. 21, 2010.
PCT Written Opinion, Jan. 21, 2012, for Henry Trong Le, International App'l No. PCT/US2010/042788, Filed Jul. 21, 2010.
Tonelli, et al., 2010, "Oral Phosphate Binders in Patients with Kidney Failure" New Engl J Med, 362: 1312-1324.
Canadian Office Action, Mar. 5, 2013, for GloboAsia LLC, Canadian Application No. 2.640,763, Filed Jul. 30, 2008.
Canadian Office Examination Report, Oct. 15, 2012, for GloboAsia LLC, Canadian Application No. 2,619,591, Filed Feb. 15, 2008.
Chinese Office Action, Aug. 30, 2012, for GloboAsia LLC, Chinese Application No. 200780003990.2, Filed Jul. 30, 2008.
Chinese Office Action, Aug. 31, 2012, for GloboAsia LLC, Chinese Application No. 200780003983.2, Filed Jul. 30, 2008.
Eurasian Notification of Readiness to Grant, Oct. 30, 2012, for Eurasian Application No. 200800593, filed Mar. 18, 2008.
European Office Action, May 9, 2012, for GloboAsia, LLC, European Application No. EP 04712312.0, filed Sep. 19, 2005.
European Office Action, Jun. 13, 2012, for GloboAsia LLC, European Application No. 06813544.1, filed Mar. 18, 2008.
European Office Action, Dec. 3, 2012, for GloboAsia, LLC, European Application No. EP 04712312.0, filed Sep. 19, 2005.
European Office Action, Dec. 20, 2012, for GloboAsia LLC, European Application No. EP11155958.9, Filed Feb. 25, 2011.
European Office Action, Feb. 1, 2013, for GloboAsia LLC, European Application No. EP 07762833.7, Filed Jun. 29, 2008.
Israeli Office Action, Jul. 4, 2012, for GloboAsia LLC, Israeli Application No. IL 192545, filed Jun. 30, 2008.
Israeli Office Action, Jul. 15, 2012, for GloboAsia LLC, Israeli Application No. IL 193099, filed Jul. 28, 2008.
Israeli Office Action, Aug. 12, 2012, for Israeli Application No. IL 189583, filed Aug. 18, 2006.
Israeli Office Action, Feb. 19, 2013, for Israeli Application No. IL 189583, filed Aug. 18, 2006.
Japanese Office Action, Jul. 31, 2012, for GloboAsia LLC, Japanese Application No. 2008-552435, Filed Jul. 30, 2008.
Japanese Office Action, Jul. 31, 2012, for GloboAsia LLC, Japanese Application No. 2008-552431, Filed Jul. 30, 2008.
Japanese Office Action, Jan. 8, 2013, for GloboAsia LLC, Japanese Application No. 2008-552435, Filed Jul. 30, 2008.
Japanese Office Action, Jan. 8, 2013, for GloboAsia LLC, Japanese Application No. 2008-552431, Filed Jul. 30, 2008.
Japanese Final Rejection, Jan. 15, 2013, for GloboAsia LLC, Japanese Application No. 2008-527177, Filed Feb. 18, 2008.
U.S. Office Action, Jan. 17, 2012, for GloboAsia, LLC for U.S. Appl. No. 12/711,679, filed Feb. 24, 2010.
U.S. Office Action, Mar. 21, 2012, for GloboAsia, LLC for U.S. Appl. No. 12/711,679, filed Feb. 24, 2010.
U.S. Office Action, Sep. 7, 2012, for GloboAsia LLC, U.S. Appl. No. 12/162,543, filed Jul. 29, 2008.
U.S. Office Action, Jan. 9, 2013, for GloboAsia, LLC for U.S. Appl. No. 12/162,558, filed Jul. 29, 2008.
U.S. Office Action, Feb. 14, 2013, for GloboAsia LLC, U.S. Appl. No. 13/661,558, filed Oct. 26, 2012.
Canadian Office Action, Jul. 9, 2013, for GloboAsia LLC, Canadian Application No. 2,640,974, Filed Jul. 30, 2008.
European Office Action, Apr. 12, 2013, for GloboAsia LLC, European Application No. 07717051.2, Filed Jun. 29, 2008.
Japanese Office Action, Jun. 25, 2013, for GloboAsia LLC, Japanese Application No. 2008-527177, Filed Feb. 18, 2008.
Mexican Office Action, Jul. 2, 2013, for GloboAsia LLC, Mexican Application No. MX/A/2011/000585, Filed Jan. 14, 2011.
Australian Office Action, Feb. 5, 2013, for GloboAsia LLC, Australian Application No. 2007210096, Filed Jul. 2, 2008.
Australian Office Action, Feb. 25, 2013, for GloboAsia LLC, Australian Application No. 2007210090, Filed Jul. 2, 2008.
Australian Office Action, Mar. 27, 2013, for GloboAsia LLC, Australian Application No. 2007210096, Filed Jul. 2, 2008.
Australian Office Action, May 20, 2013, for GloboAsia LLC, Australian Application No. 2007210096, Filed Jul. 2, 2008
Australian Office Action, Apr. 24, 2013, for GloboAsia LLC, Australian Application No. 2007210090, Filed Jul. 2, 2008.
Chinese Office Action, Mar. 18, 2013, for GloboAsia LLC, Chinese Application No. 200780003983.2, Filed Jul. 30, 2008.
Chinese Office Action, Mar. 18, 2013, for GloboAsia LLC, Chinese Application No. 200780003990.2, Filed Jul. 30, 2008.
Korean Office Action, Dec. 17, 2012, for GloboAsia LLC, Korean Application No. 10-2008-7018634, Filed Jul. 29, 2008.
Korean Office Action, Jun. 28, 2013, for GloboAsia LLC, Korean Application No. 10-2008-7018634, Filed Jul. 29, 2008.
Korean Office Action, Feb. 8, 2013, for GloboAsia LLC, Korean Application No. 10-2008-7006131, Filed Mar. 13, 2008.
Korean Office Action, Jun. 28, 2013, for GloboAsia LLC, Korean Application No. 10-2008-7018633, Filed Jul. 29, 2008.
Korean Office Action, Dec. 17, 2012, for GloboAsia LLC, Korean Application No. 10-2008-7018633, Filed Jul. 29, 2008
Philippine Office Action, Oct. 15, 2012, for GloboAsia LLC, Philippine Application No. 1-2005-501521, Filed Aug. 19, 2005.
Philippine Office Action, Jul. 3, 2013, for GloboAsia LLC, Philippine Application No. 1-2005-501521, Filed Aug. 19, 2005.
Bernacca et al., "Chemical modification of bovine pericardium and its effect on calcification in the rat subdermal model." Biomaterials. 1992; vol. 13(6):345-52.

* cited by examiner

FERRIC ORGANIC COMPOUNDS, USES THEREOF AND METHODS OF MAKING SAME

This application is a Continuation of U.S. Ser. No. 12/711,679, filed Feb. 24, 2010 (now allowed), which is a Continuation of U.S. Ser. No. 11/206,981 (now U.S. Pat. No. 7,767,851), filed Aug. 18, 2005, which is a Continuation-in-part of International App'l No. PCT/US2004/004646, filed Feb. 18, 2004, which claims benefit of U.S. Ser. No. 60/462,684, filed Apr. 15, 2003, and U.S. Ser. No. 60/447,690, filed Feb. 19, 2003. The entire contents and disclosures of the preceding applications are hereby incorporated by reference into this application.

Throughout this application, various publications are referenced. Disclosures of these publications in their entireties are hereby incorporated by reference into this application to more fully describe the state of the art to which this invention pertains.

TECHNICAL FIELD

This invention relates to ferric organic compounds, such as ferric citrate, methods of making the ferric organic compounds, and uses of the ferric organic compounds in the treatment of various disorders.

BACKGROUND OF THE INVENTION

1) Uses of Iron Compounds

Ferric iron containing compounds are useful in the treatment of a number of disorders, including, but not limited to, hyperphosphatemia and metabolic acidosis. Previous studies and inventions have reported the use of ferric compounds in binding with dietary phosphates, and such ferric compounds are potentially useful for the treatment of hyperphosphatemia in renal failure patients (U.S. Pat. No. 5,753,706, 1998; U.S. Pat. No. 6,903,235, 2005; CN 1315174, 2001; Yang W. C., et al., *Nephrol. Dial. Transplant* 17:265:270 (2002)). Elevated amounts of phosphate in the blood can be removed by administering compounds such as ferric citrate. Once in solution, the ferric iron binds phosphate, and the ferric phosphate compounds precipitate in the gastrointestinal tract, resulting in effective removal of dietary phosphate from the body. It is also believed that the absorbed citrate from ferric citrate is converted to bicarbonate which corrects metabolic acidosis, a condition common in renal failure patients.

U.S. Pat. No. 5,753,706 discloses the use of ferric containing compounds including ferric citrate and ferric acetate in the crystalline form, in an orally effective 1 gram dosage form, to bind to soluble dietary phosphate, causing precipitation of phosphate as ferric or ferrous phosphates in the gastrointestinal tract thus preventing oral absorption of soluble phosphates from dietary sources. Since the binding of ferric ions to soluble phosphate in the gastrointestinal tract would require dissolution of the orally administered ferric citrate, and since the rate of dissolution of crystalline ferric citrate is slow (over 10-12 hours at 37° C.), oral administration of a substantially large dose of 1 g of ferric citrate is required. A related Chinese patent application (CN 1315174) also discloses a similar use of ferric citrate and related compounds in an oral solution dosage form for the treatment of hyperphosphatemia in renal failure patients.

2) Solution Chemistry of Fe(III) Compounds

Fe(III) is a lewis acid and is chemically less soluble in the stomach at pH normally below 5 than at intestinal pH normally above 7. The stomach is believed to be an important site of action for the dissolution of Fe(III) compounds. It is also believed that the stomach is also an important site of action for Fe(III) to mediate its action in binding to dietary phosphates, preventing phosphate from reaching the intestine and thus reducing the absorption of phosphates from the intestine.

SUMMARY OF THE INVENTION

In accordance with these and other objects of the invention, a brief summary of the present invention is presented. Some simplifications and omission may be made in the following summary, which is intended to highlight and introduce some aspects of the present invention, but not to limit its scope. Detailed descriptions of a preferred exemplary embodiment adequate to allow those of ordinary skill in the art to make and use the invention concepts will follow in later sections.

This invention relates to novel forms of ferric organic compounds, methods of making these compounds, and uses of these compounds in the treatment of various disorders, including, but not limited to, hyperphosphatemia and metabolic acidosis.

The novel forms of ferric organic compounds are synthesized by adding an alkaline metal hydroxide to a water soluble ferric iron salt. The alkaline metal hydroxide can comprise sodium hydroxide, potassium hydroxide, or any other suitable alkaline metal hydroxide. The soluble ferric iron salt can comprise ferric chloride hexahydrate, or any other suitable ferric iron salt. The alkaline metal hydroxide is added at a specific rate and temperature to form a uniform polyiron oxo colloidal suspension. The colloidal suspension is then washed, and solid crystalline organic acid is added at a specific temperature to form the ferric organic compound in solution. The organic acid can comprise citric acid, acetic acid, isocitric acid, succinic acid, fumaric acid, tartaric acid, or any other suitable organic acid. The novel forms of the ferric organic compounds are precipitated out of solution using an organic solvent. The organic solvent can comprise ethanol, methanol, butanol, acetone, isopropyl alcohol, tetrahydrofuran, or any other suitable organic solvent. The resulting novel forms of the ferric organic compounds have an enhanced dissolution rate.

In one embodiment, the novel form of ferric organic compound comprises a novel form of ferric citrate. The novel form of ferric citrate is synthesized by adding sodium hydroxide at a specific rate and temperature to ferric chloride hexahydrate to form a uniform colloidal suspension of ferric hydroxide. Solid crystalline citric acid is added to the colloidal suspension and heated to a specific temperature range to form ferric citrate in solution. The novel form of ferric citrate is precipitated out of solution using an organic solvent.

The novel form of ferric citrate has the formula $C_6H_5O_7Fe$ and has novel physical properties as determined by dissolution rates. The compound can have an intrinsic dissolution rate range, as determined by USP (United States Pharmacopeia) intrinsic dissolution assay in water, between 1.9 to 4.0 $mg/cm^2/min$. The novel form of ferric citrate is more aqueously soluble in a wider range of pH than commercially available forms of ferric citrate. The novel form of ferric citrate can have a large active surface area compared to commercially available forms of ferric organic compounds or complexes.

Because it is more soluble, the novel form of ferric organic compounds, including novel forms of ferric citrate, can be used to more effectively deliver ferric organic compounds by the route of oral administration to patients suffering from illnesses which are responsive to treatment with ferric organic compounds, including, but not limited to, hyperphosphatemia and metabolic acidosis.

This invention relates to use of the novel form of ferric organic compounds, including novel forms of ferric citrate to treat patients suffering from disorders responsive to ferric organic compound treatment.

This invention also relates to methods of treating patients suffering from disorders responsive to ferric organic compound treatment by administering a therapeutically effective amount of ferric organic compound to the patients.

This invention further relates to a composition for treating hyperphosphatemia in a subject, comprising an effective amount of ferric citrate. In an embodiment, the subject is a human being. In another embodiment, the amount of ferric citrate effective in treating hyperphosphatemia is between 3 to 6 grams/day. In a further embodiment, the effective amount is 3 or 4.5 grams/day.

This invention further relates to a method for treating hyperphosphatemia in a subject, comprising administering to said subject an effective amount of ferric citrate. In an embodiment, the subject is a human being. In another embodiment, the amount of ferric citrate effective in treating hyperphosphatemia in a subject is between 3 to 6 grams/day. In a further embodiment, the effective amount is or 4.5 grams/day. It will be within the knowledge and abilities of a person having ordinary skill in the art to perform a dose-ranging study to determine the effective amount of ferric organic compounds or ferric citrate of the present invention.

DETAILED DESCRIPTION OF THE FIGURES

In drawings which illustrate specific embodiments of the invention, but which should not be construed as restricting the spirit or scope of the invention in any way:

Figure 3:
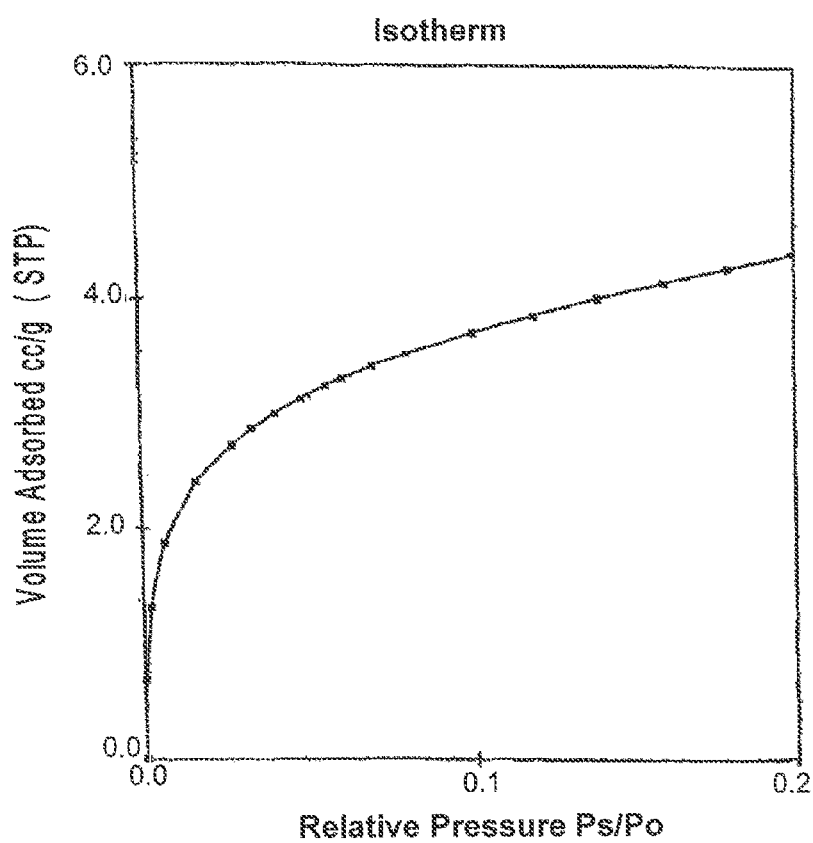

FIG. 3 is an isotherm graph of volume adsorbed vs. relative pressure demonstrating BET active surface area of the novel form of ferric citrate. Produced by Coulter SA 3100 (Serial No. z11017; Software Version 2.13; Elapsed time: 29 min.; Outgas time: 60 min.; Outgas temperature: 40° C.)

Figure 4:
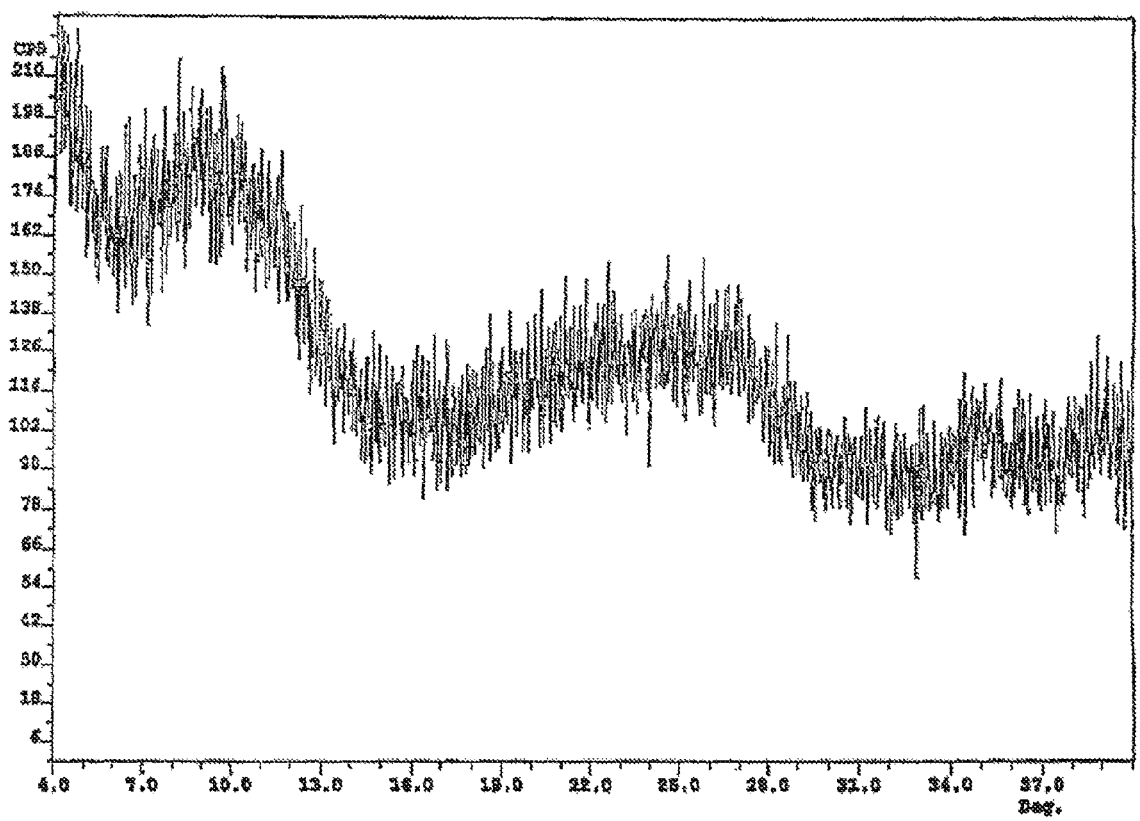

FIG. 4 is an X-ray diffraction spectra of the novel form of ferric citrate. Range: 4.00 to 40.00 (Deg); Step Scan Rate: 0.02 Deg/min.

Figure 5:
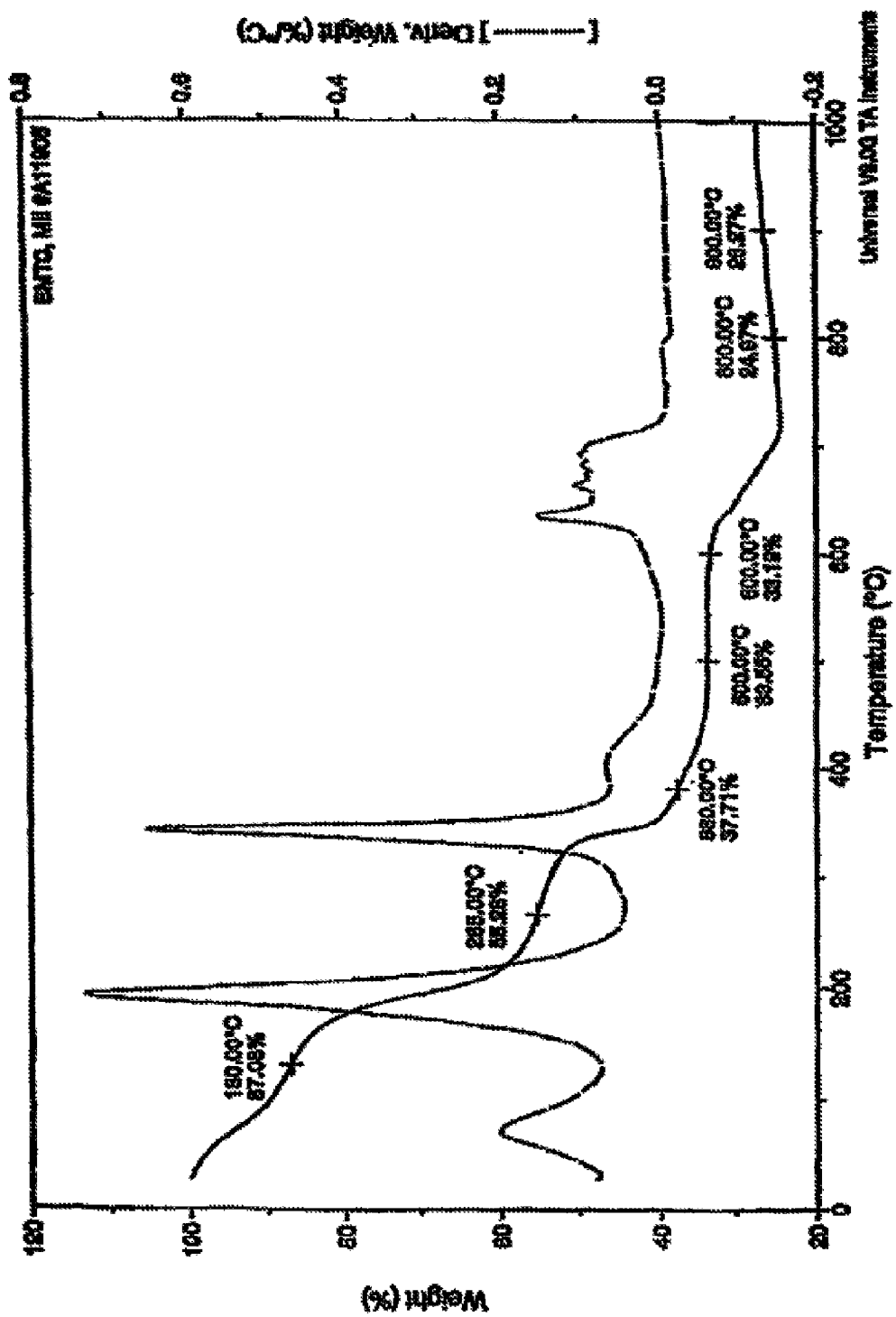

FIG. 5 is a thermogravimetric analysis of the novel form of ferric citrate. Method: Heating 10° C./MIN, $N_2$@40 CC/MIN; Size: 10.5480 mg.

DETAILED DESCRIPTION OF THE INVENTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

This invention provides a method of synthesizing a form of ferric organic compound which comprises obtaining a ferric iron salt; adding an alkaline metal hydroxide to the ferric iron salt at a rate and temperature effective to produce a uniform polyiron oxo suspension; isolating a precipitate from the suspension; adding an organic acid to the precipitate; forming a ferric-organic acid solution by heating the organic acid and the precipitate; and precipitating the form of ferric organic compound from the ferric-organic acid solution by adding an organic solvent to the solution.

In an embodiment, the alkaline metal hydroxide is added at a rate of less than 20 ml/min. In another embodiment, the alkaline metal hydroxide is added at a rate of between about 10 ml/min and about 20 ml/min. In a preferred embodiment, a nominal rate of 10 to 20 ml/min is preferred.

In an embodiment, the alkaline metal hydroxide is added to the ferric iron salt at a temperature of less than 40° C. In another embodiment, the alkaline metal hydroxide is added to the ferric iron salt at a temperature between about 10° C. and about 40° C. In a preferred embodiment, a nominal temperature of 30° C. is preferred.

In an embodiment, heating the organic acid and the precipitate comprises heating the organic acid and the precipitate to a temperature between about 75° C. to about 95° C. In a preferred embodiment, the range is between about 80° C. and about 90° C. In another preferred embodiment, a nominal temperature of 85° C. is preferred. In an embodiment, precipitating the form of ferric organic compound from the ferric-organic acid solution by adding an organic solvent to the solution comprises cooling the ferric-organic acid solution to less than 30° C. before adding the organic solvent. In a preferred embodiment, the ferric-organic acid solution is cooled to a nominal temperature of 20° C. In an embodiment, cooling the ferric-organic acid solution comprises cooling the ferric-organic acid solution to a temperature between about 10° C. and about 30° C. In a preferred embodiment, the ferric-organic acid solution is cooled to a nominal temperature of 20° C.

In an embodiment, the ferric iron salt comprises ferric chloride hexahydrate.

In an embodiment, the organic acid includes but is not limited to succinic acid, fumaric acid or tartaric acid. In another embodiment, the organic acid comprises citric acid.

In an embodiment, the alkaline metal hydroxide includes but is not limited to sodium hydroxide or potassium hydroxide. In another embodiment, the alkaline metal hydroxide comprises sodium hydroxide.

In an embodiment, the organic solvent includes but is not limited to ethanol, methanol, butanol, isopropyl alcohol, acetone or tetrahydrofuran.

This invention provides a method of synthesizing a form of ferric citrate which comprises obtaining ferric chloride hexahydrate; adding sodium hydroxide to the ferric chloride hexahydrate at a rate and temperature effective to produce a uniform polyiron oxo suspension; isolating a precipitate from the suspension; adding crystalline citric acid to the precipitate; forming a ferric-citric acid solution by heating the citric acid and the precipitate; and precipitating the form of ferric citrate from the ferric-citric acid solution by adding an organic solvent to the solution.

In an embodiment, sodium hydroxide is added to ferric chloride hexahydrate at a rate of less than 20 ml/min. In another embodiment, sodium hydroxide is added to ferric chloride hexahydrate at a rate of between about 10 ml/min and about 20 ml/min. In a preferred embodiment, a nominal rate of 10 to 20 ml/min is preferred.

In an embodiment, sodium hydroxide is added to ferric chloride hexahydrate at a temperature of less than 40° C. In another embodiment, sodium hydroxide is added to ferric chloride hexahydrate at a temperature between about 10° C. and about 40° C. In a preferred embodiment, a nominal temperature of 30° C. is preferred.

In an embodiment, the ferric-citric acid solution is formed by heating the citric acid and the precipitate to a temperature between about 75° C. to about 95° C. In a preferred embodiment, the range is between about 80° C. and about 90° C. In another preferred embodiment, a nominal temperature of 85° C. is preferred.

In an embodiment, precipitating the form of ferric citrate from the ferric-citric acid solution by adding an organic solvent to the solution comprises cooling the ferric-citric acid solution to less than 30° C. before adding the organic solvent. In a preferred embodiment, the ferric-organic acid solution is cooled to a nominal temperature of 20° C.

In an embodiment, cooling the ferric-citric acid solution comprises cooling the ferric-citric acid solution to a temperature between about 10° C. and about 30° C. In a preferred embodiment, the ferric-organic acid solution is cooled to a nominal temperature of 20° C.

In an embodiment, the organic solvent includes but is not limited to ethanol, methanol, butanol, isopropyl alcohol, acetone or tetrahydrofuran.

This invention provides a use of a form of ferric organic compound or ferric citrate as describe above for treating a subject suffering from a disorder responsive to ferric organic compound therapy. In an embodiment, the subject is a human being. In another embodiment, the disorder includes but is not limited to hyperphosphatemia or metabolic acidosis. Chen et al., New Phosphate Binding Agent: Ferric Compounds. J Am Soc Nephrol. 10(6):1274-80, 1999, reported that Ferric salts, such as ferric citrate, decrease net intestinal phosphate absorption. Yang et al., An open-label, crossover study of a new phosphate-binding agent in haemodialysis patients: ferric citrate. Nephrol Dial Transplant. 17(2):265-70, 2002, reported that ferric citrate is effective and well tolerated as a treatment for hyperphosphatemia in patients.

This invention provides a method of treating a subject suffering from a disorder responsive to ferric organic compound therapy comprising administering to the subject a therapeutically effective amount of a ferric organic compound as described above. In an embodiment, the subject is a human being. In another embodiment, the ferric organic compound is ferric citrate. In a further embodiment, the disorder includes but is not limited to hyperphosphatemia or metabolic acidosis.

This invention provides a form of a ferric organic compound having an enhanced dissolution rate. In an embodiment, the said organic compound includes but is not limited to citric acid, acetic acid, isocitric acid, succinic acid, fumaric acid, tartaric acid or other related organic compounds. In another embodiment, the said ferric organic compound has a large active surface area compared to conventional ferric organic compounds.

This invention provides a form of ferric citrate having the formula $C_6H_5O_7Fe$ and/or having physical properties as determined by dissolution rates. In an embodiment, the dissolution rate, as determined by USP intrinsic dissolution assay in water, is between 1.9 to 4.0 mg/cm2/min.

This invention provides a form of ferric citrate having a BET (Brunauer Emmett Teller) active surface area exceeding 16 sq.m/g and a BET active surface area isotherm as shown in FIG. 3.

This invention provides a form of ferric citrate having the x-ray diffraction pattern shown in FIG. 4.

This invention provides a form of ferric citrate having three transition temperatures as determined by thermogravimetric analysis (TGA) and having a TGA profile as shown in FIG. 5.

This invention provides a form of ferric citrate, wherein the form of ferric citrate has a large active surface area compared to conventional ferric organic compound complexes.

This invention provides a use of a form of ferric organic compound or ferric citrate to treat a subject suffering from a disorder responsive to ferric organic compound therapy. In an embodiment, the disorder includes but is not limited to hyperphosphatemia or metabolic acidosis.

This invention provides a method of treating a subject suffering from a disorder responsive to ferric organic compound therapy comprising administering to the subject a therapeutically effective amount of a form of ferric organic compound or ferric citrate as described above. In an embodiment, the disorder includes but is not limited to hyperphosphatemia or metabolic acidosis.

This invention provides a form of ferric organic compound or ferric citrate as describe above, wherein said form of ferric organic compound or ferric citrate is in an orally administrable form which includes, but is not limited to, a powder, a suspension, an emulsion, a capsule, a granule, a troche, a pill, a liquid, a spirit or a syrup. In an embodiment, the ferric organic compound or ferric citrate is in a form or in an acceptable carrier suitable for topical, sublingual, parenteral or gastrointestinal administration, or aerosolization.

This invention provides a composition comprising a form of ferric organic compound or ferric citrate as describe above and a suitable carrier.

As used herein, the term suitable carrier includes, but not limited to, any suitable carrier for administering pharmaceutical compositions known to those of ordinary skill in the art. The type of carrier will vary depending on the mode of administration.

With regards to compositions for parenteral administration (e.g. subcutaneous injections), the term suitable carrier includes but not limited to water, saline, alcohol, a fat, a wax or a buffer.

With regards to compositions for oral administration, the term suitable carrier includes but not limited to any of the above carriers or a solid carrier, such as mannitol, lactose, starch, magnesium stearate, sodium saccharine, talcum, cellulose, glucose, sucrose, and magnesium carbonate.

Biodegradable microspheres (e.g., polylactate polyglycolate) may also be employed as carriers for the pharmaceutical compositions of this invention.

This invention provides a pharmaceutical composition comprising a form of ferric organic compound or ferric citrate as describe above and a pharmaceutically acceptable carrier. In another embodiment, the pharmaceutically acceptable carrier comprises a controlled release formulation.

This invention provides a pharmaceutical composition comprising an effective amount of a form of ferric organic compound or ferric citrate as describe above for treating disorders responsive to ferric organic compound therapy. In an embodiment, the disorder includes but is not limited to hyperphosphatemia and metabolic acidosis.

As used herein, pharmaceutically acceptable carriers includes, but is not limited to, a liquid, an aerosol, a capsule, a tablet, a pill, a powder, a gel, an ointment, a cream, a granule, water, phosphate buffered saline, Ringer's solution, dextrose solution, serum-containing solutions, Hank's solution, other aqueous physiologically balanced solutions, oils, esters, glycols, biocompatible polymers, polymeric matrices, capsules, microcapsules, microparticles, bolus preparations, osmotic pumps, diffusion devices, liposomes, lipospheres, cells or cellular membranes.

1. General Method of Synthesis of Novel Forms of Ferric Organic Compounds

Figure 1:
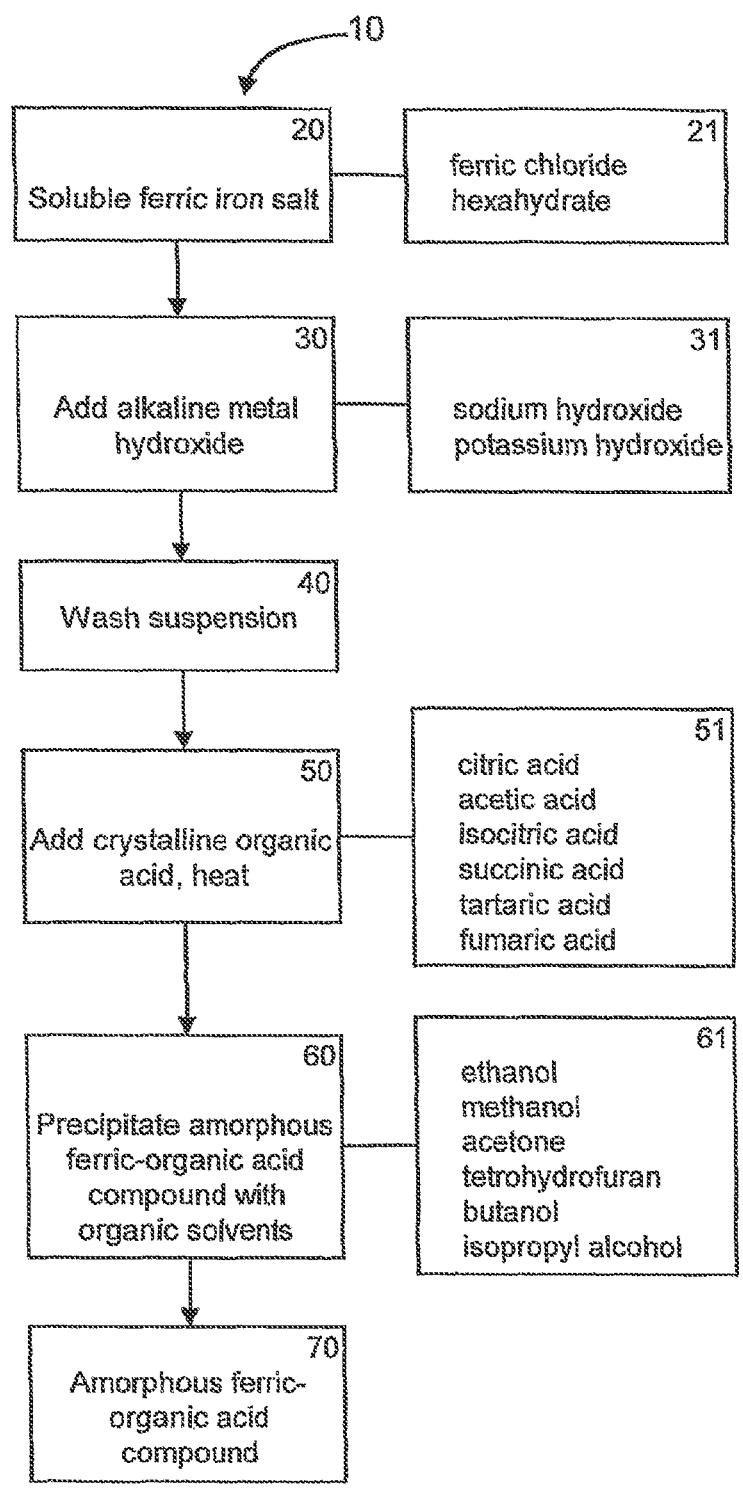
FIG. 1 is a schematic diagram outlining the method of making novel forms of ferric organic compounds according to the invention.

Referring to FIG. 1, synthesis scheme 10 is a general method for synthesizing novel forms of ferric organic compounds. The starting materials, as indicated in box 20, comprise soluble ferric iron salts. The soluble ferric iron salts can comprise ferric chloride hexahydrate ($FeCl_3 6H_2O$), as indicated in box 21, or any other suitable soluble ferric iron salt. Next, an alkaline metal hydroxide (box 30) is added at a specific rate and temperature to the soluble ferric iron salt. The addition of the alkaline metal hydroxide at a specific rate, preferably between about 10 ml/min and about 20 ml/min, and temperature range, preferably below 40° C., results in the formation of a uniform polyiron oxo colloidal suspension. The alkaline metal hydroxide can comprise sodium hydroxide, potassium hydroxide, or any other suitable alkaline metal hydroxide as indicated in box 31. The colloidal suspension precipitate is collected and rinsed (box 40) with distilled water to remove any soluble impurities. After rinsing, the precipitate is resuspended and, as indicated in box 50, crystalline organic acid is added to the precipitate and heated to a particular temperature range, preferably between about 80° C. to about 90° C. The organic acid can comprise any suitable organic acid. Box 51 lists some of the possible organic acids which can be used, including, but not limited to, citric acid, acetic acid, isocitric acid, succinic acid, fumaric acid, and tartaric acid. The addition of the organic acid allows the acid to form complexes with the precipitate in solution. At box 60, the ferric organic compound is precipitated out of solution with an organic solvent to form a novel form of ferric organic compound (box 70). Various organic solvents can be used, including, but not limited to, the solvents described in box 61, such as ethanol, methanol, butanol, acetone, isopropyl alcohol, tetrahydrofuran, or any other suitable organic solvent.

2. Solubility Profile of Novel Forms of Ferric Organic Compounds

The inventors have found that the novel forms of ferric organic compounds produced according to the methods described above are more soluble than commercially available ferric organic compounds, over a wider range of pH levels. This increase in solubility of the novel ferric organic compounds is believed to be a result of the unique significantly large active surface area of the novel forms of ferric organic compounds. For example, at pH 8.0, the intrinsic dissolution rate of novel form of ferric citrate is 3.08 times greater than the commercially available ferric citrate. See Table 3.

3. Use of Novel Forms of Ferric Organic Compounds in the Treatment of Disorders The novel forms of ferric organic compounds are useful in the treatment of hyperphosphatemia, metabolic acidosis, and any other disorders responsive to ferric organic compound therapy. Because the novel forms of ferric organic compounds are more soluble than commercially available ferric organic compounds, smaller amounts of the ferric organic compounds can be used to effectively treat patients suffering from such disorders.

Improved aqueous solubility is particularly relevant to the use of the novel forms of ferric organic compounds in the treatment of disorders responsive to ferric organic compound therapy. Because the novel forms of ferric organic compounds are more soluble, they will be more effective when taken orally, and therefore can be taken in lower doses. The novel forms of ferric organic compounds are more soluble over a wider pH range than commercially available ferric organic compounds, therefore the novel forms of ferric organic compounds can be more effective by being soluble in the small intestine. For example, in an experiment simulating the alkaline condition in the small intestine, the novel form of ferric citrate showed better dissolution rate than the commercially available ferric citrate. It is suggested that the novel form of ferric citrate can be more effective by being more soluble in the small intestine. See Table 3. As a result, patients can take lower doses of medication with lower incidences of side effects.

In one embodiment of the invention, the novel form of ferric citrate has a significantly higher rate of aqueous solubility under physiological conditions than commercially available forms of ferric citrate, and therefore the novel form is believed to provide a significant improvement in the orally effective use of ferric citrate at a reduced dosage. By reducing the orally effective dose of ferric citrate, it is believed that the novel form of ferric citrate will provide a lower incidence of ulcerative gastrointestinal adverse effects associated with commercially available ferric citrate compounds. In addition, it is believed that the increased rate of dissolution of the novel form of ferric citrate will provide a more rapid onset of action in binding to dietary phosphate.

The novel forms of ferric organic compounds can be administered in a number of forms, including orally administrable forms, which can comprise the novel forms of ferric organic compounds alone or in combination with a pharmaceutically acceptable carrier. The orally administrable form includes, but is not limited to, a tablet, a powder, a suspension, an emulsion, a capsule, a granule, a troche, a pill, a liquid, a spirit, or a syrup. The composition can be administered to human beings or other animals suffering from illnesses responsive to ferric organic compound therapy.

EXAMPLES

In examples which are intended to illustrate embodiments of the invention but which are not intended to limit the scope of the invention:

1) Method of Making a Novel Form of Ferric Citrate

In one embodiment of the invention, the starting materials for making a novel form of ferric citrate comprise a 1.85M solution of ferric chloride hexahydrate ($FeCl_3 6H_2O$). A volume of 5M sodium hydroxide necessary to produce a 1:3 ratio of ferric iron to hydroxide ion is added to the ferric chloride hexahydrate solution at a rate of less than 20 ml per minute, preferably between about 10 ml per minute and about 20 ml per minute. The temperature of the mixture is maintained below 40° C., preferably between about 10° C. to about 40° C., while the sodium hydroxide is added to form a polyiron oxide colloidal suspension of ferric hydroxide. The pH of the suspension is measured while the sodium hydroxide is added. Once the pH is above 7.0, the suspension is cooled until it is less than 30° C., preferably between about 10° C. to about 30° C. The suspension is then filtered through a 1 mm pore filter to breakup aggregates and remove large particles of ferric hydroxide precipitate. The filtered ferric hydroxide suspension is then centrifuged. The supernatant is discarded, then the precipitated ferric hydroxide is centrifuged again to remove any remaining supernatant. The ferric hydroxide precipitate is then resuspended with distilled water. The centrifugation-resuspension steps are repeated two more times to wash the ferric hydroxide precipitate and remove water soluble impurities. The resulting ferric hydroxide precipitate is then homogenized.

An amount of citric acid necessary to produce a 1:1 ratio of ferric iron to citrate is added to the precipitate. The mixture is heated to between about 80° C. to about 90° C. in an oil bath until the color of the mixture changes from orange-brown to a clear black-brown, or until all of the ferric hydroxide precipitate is dissolved. The reaction is cooled until it is less than 30° C., preferably between about 10° C. to about 30° C., and the pH is measured to determine that it is within 0.8 and 1.5. The reaction is centrifuged, and the supernatant is collected.

The novel form of ferric citrate is precipitated from the supernatant by adding 5 volumes of organic solvent. Various organic solvents can be used, including ethanol, methanol, butanol, acetone, isopropyl alcohol, or tetrahydrofuran. Table 1 below lists the relative amounts of ferric citrate formed in solution using various solvents. Once the solvent is added, the mixture is stirred until a light beige precipitate forms. The suspension is centrifuged and the supernatant is discarded. The precipitate is washed and centrifuged with the solvent two more times. The precipitate is then dried in a vacuum oven for 8 to 16 hours at ambient temperature or by any other suitable industrial processes such as fluidized-bed drying. The dried precipitate is ground with a mortar and pestle and dried for another 8 to 24 hours at ambient temperature. The fine precipitate is finely ground by milling again and screened through a 45 mesh size (35 micron) sieve. The novel form of ferric citrate powder is dried in the vacuum oven again or fluidized-bed drying again and dried at ambient temperature until 1 hour of drying leads to less than 0.25% loss in weight.

TABLE 1

Comparison of relative percentage of novel form of ferric citrate formed by different organic solvents

| Solvent | Relative % of Novel Form of Ferric Citrate Formed in Solution |
| --- | --- |
| ferric citrate | 100 |
| isopropyl alcohol | 89.7 |
| tetrahydrofuran | 90.6 |
| butanol | 99.8 |
| methanol | 101.2 |
| acetone | 99.8 |
| ethanol | 95.8 |

The following chemical equations represent the chemical reactions described in the specific embodiment of the method for making the novel form of ferric citrate:

$$FeCl_3 + 3NaOH \rightarrow Fe(OH)_3 + 3NaCl \quad (1)$$

$$Fe(OH)_3 + C_6H_8O_7 \rightarrow Fe(C_6H_5O_7) + 3H_2O \quad (2).$$

2) Physical Properties of Novel Form of Ferric Citrate

The chemical purity of the novel form of ferric citrate was ascertained by negative-ion liquid chromatography or mass spectrometry (LC/MS) flow-injection method which provided measurement of all mass ions present in solution. Specifically, the mass ions at m/z 243.6 for the novel form of ferric citrate and at m/z 190.6 for citric acid amongst other related and non-related ions in solution were observed. The use of LC/MS analysis also enabled the observation of a number of ferric citrate related and non-related substances and permitted the determination of the relative purity of the novel form of ferric citrate amongst the minor impurities. Such information is critical for application of the novel form of ferric citrate as pharmaceutical grade material. The representative chemical purity of the novel form of ferric citrate from three process batches are presented in Table 2.

TABLE 2

Representative chemical purity of novel form of ferric citrate

| Components of Novel form of Ferric citrate | Percent w/w anhydrous basis | | |
| --- | --- | --- | --- |
| Purity of solid state ferric citrate | 99.4% | 99.6% | 99.5% |
| Assay content purity of ferric citrate and ferric citrate water adduct in solution state | 73.1% | 78.3% | 76.2% |
| Assay content of citric acid in solution state | 10.3% | 10.0% | 8.0% |
| Assay content of ferric citrate related substances in solution state | 26.3% | 21.3% | 23.3% |
| Assay content of ferric citrate non-related substances in solution state | 0.6% | 0.4% | 0.5% |

The intrinsic dissolution rates of commercially available ferric citrate were compared with the novel form of ferric citrate. The intrinsic dissolution rate is defined as the dissolution rate of pure substances under the condition of constant surface area. The dissolution rate and bioavailability of a drug substance is influence by its solid state properties: crystallinity, amorphism, polymorphism, hydration, solvation, particle size and particle surface area. The measured intrinsic dissolution rate is dependent on these solid-state properties and is typically determined by exposing a constant surface area of a material to an appropriate dissolution medium while maintaining constant temperature, stirring rate, and pH. The intrinsic dissolution rates are presented in Table 3.

TABLE 3

Intrinsic dissolution rates of ferric citrate at 37° C. in solutions of pH 8

| Sample | Rate of Acetone Addition (ml/min) | Intrinsic Dissolution Rates (mg/cm2/min) | Mean Intrinsic Dissolution Rates (mg/cm2/min) |
| --- | --- | --- | --- |
| RFS-12 (sigma/ commercially available) | 10.0 | 0.83 | 0.83 |
| STM-134 (reference material) | 10.0 | 1.88 | 3.08 |
| PAN031203A (experimental batch 1) | 10.0 | 3.82 | |
| PAN031203B (experimental batch 2) | 10.0 | 4.00 | |
| PAN031203C (experimental batch 3) | 9.5 | 2.68 | |
| PAN031203D (experimental batch 4) | 40 | 2.95 | |
| PAN031203E (experimental batch 5) | 4.4 | 3.13 | |

Figure 2:
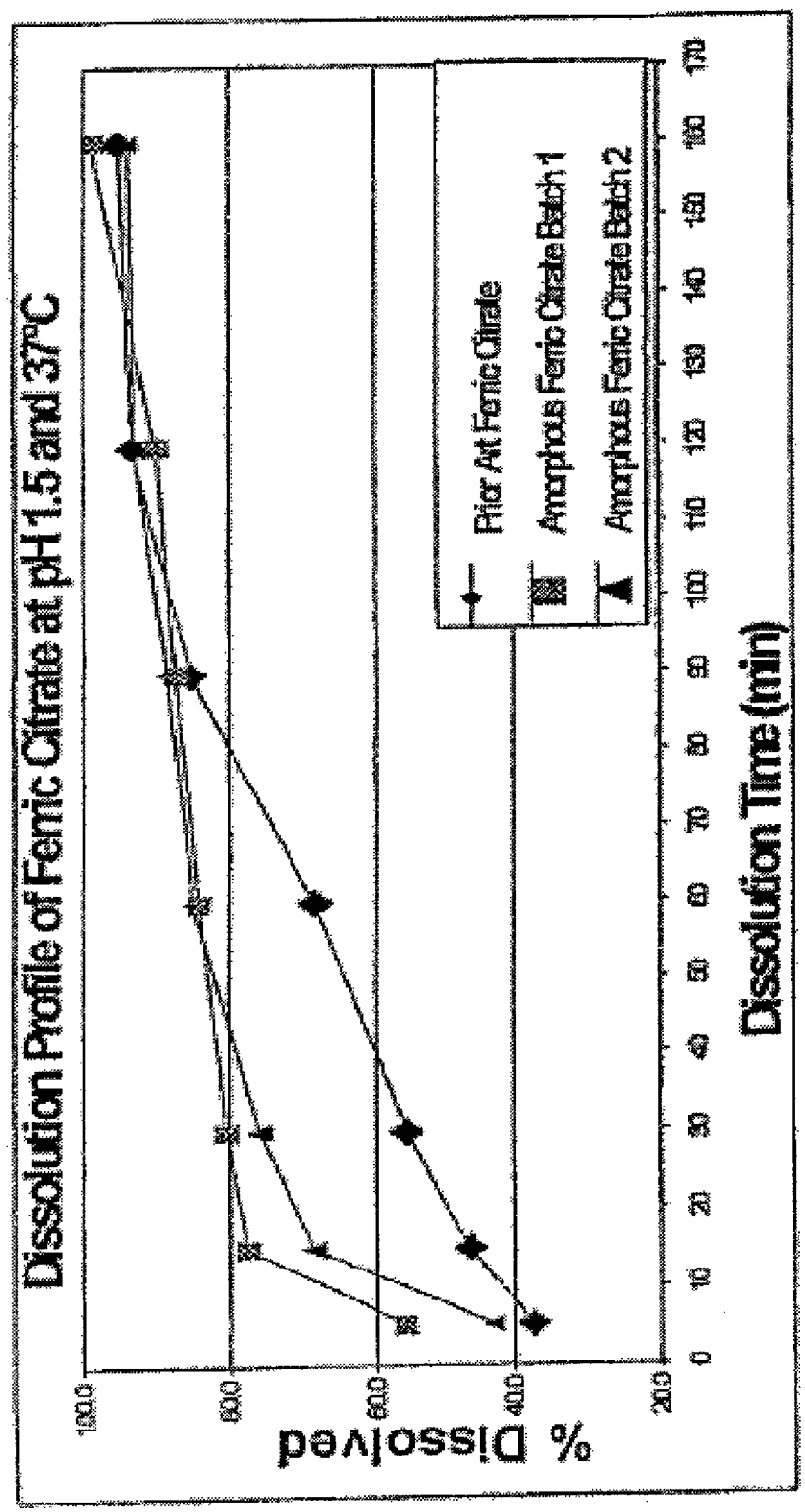
FIG. 2 is a plot of the dissolution profile of the novel form of ferric citrate of the invention compared to a commercially available compound.

FIG. 2 is a graph which compares the dissolution profile of the novel form of ferric citrate to the dissolution profile of commercially available ferric citrate compounds.

The intrinsic dissolution rates of the novel form of ferric citrate produced by the method of the invention, on average, are approximately 3.8 times greater than that determined for a commercially available ferric citrate material. This increase in dissolution rate of the novel form of ferric citrate is believed to be a result of the significantly large active surface area of the novel form of ferric citrate compared to commercially available materials. For example, the BET active surface area of novel form of ferric citrate is at least 16 times larger than the commercially available ferric citrate. See Table 4.

A BET active surface area isotherm of the novel form of ferric citrate is shown in FIG. 3. The analysis of active surface area is based on BET theory which describes the phenomenon of mass and energy interaction and phase changes during gas adsorption onto solid surfaces and in pore spaces. In BET active surface area measurement, the volume of a monolayer of gas is determined which allows the surface area of the sample to be determined using the area occupied by a single layer of adsorbed gas molecule. Table 4 is a comparison of the active surface area of the novel form of ferric citrate compared to the active surface area of commercially available ferric citrate compounds.

TABLE 4

BET active surface areas of various forms of ferric citrate

| Sample | Mean Dissolution Rates (mg/cm2/min) | BET Active Surface Area |
| --- | --- | --- |
| RFS-12-1 (sigma/commercially available) | 0.76 | 0.61 |
| RFS-12-2 (sigma/commercially available) | | |
| STM-134-1 (reference material 1) | 2.47 | 16.17 |
| STM-134-2 (reference material 2) | | |
| STM-182-1 (lab-scale 500 g batch 1) | 2.61 | 19.85 |
| STM-182-2 (lab-scale 500 g batch 2) | | |

The x-ray diffraction spectra of the novel form of ferric citrate are presented in FIG. 4, showing diffraction features characteristics of crystalline materials. The thermogravimetric analysis of the novel form of ferric citrate is presented in FIG. 5, showing heat absorption isotherms characteristics of the novel material.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. Ferric citrate having an intrinsic dissolution rate of 1.88-4.0 mg/cm$^2$/min.

2. The ferric citrate of claim 1, wherein the intrinsic dissolution rate is measured by USP (United States Pharmacopeia) intrinsic dissolution assay in water.

3. The ferric citrate of claim 1, wherein the intrinsic dissolution rate is selected from 1.88 mg/cm$^2$/min, 2.68 mg/cm$^2$/min, 3.82 mg/cm$^2$/min and 4.00 mg/cm$^2$/min.

4. The ferric citrate of claim 1, having the formula $C_6H_5O_7Fe$.

5. The ferric citrate of claim 1, which is in an orally administrable form.

6. The ferric citrate of claim 5, wherein the orally administrable form is selected from a tablet, a powder, a suspension, an emulsion, a capsule, a granule, a troche, a pill, a liquid, a spirit and a syrup.

7. The ferric citrate of claim 5, wherein the orally administrable form is a tablet.

8. A method of treating hyperphosphatemia comprising administering ferric citrate having an intrinsic dissolution rate of 1.88-4.0 mg/cm$^2$/min to a patient in need of such treatment.

9. A method of treating metabolic acidosis comprising administering ferric citrate having an intrinsic dissolution rate of 1.88-4.0 mg/cm$^2$/min to a patient in need of such treatment.

10. A pharmaceutical composition comprising ferric citrate having an intrinsic dissolution rate of 1.88-4.0 mg/cm$^2$/min and a suitable carrier.

11. The pharmaceutical composition of claim 10, wherein the intrinsic dissolution rate is measured by USP (United States Pharmacopeia) intrinsic dissolution assay in water.

12. The pharmaceutical composition of claim 10, wherein the intrinsic dissolution rate is selected from 1.88 mg/cm$^2$/min, 2.68 mg/cm$^2$/min, 3.82 mg/cm$^2$/min and 4.00 mg/cm$^2$/min.

13. The pharmaceutical composition of claim 10, wherein the ferric citrate has the formula $C_6H_5O_7Fe$.

14. The pharmaceutical composition of claim 10, wherein the composition is in an orally administrable form.

15. The pharmaceutical composition of claim 14, wherein the orally administrable form is selected from a tablet, a powder, a suspension, an emulsion, a capsule, a granule, a troche, a pill, a liquid, a spirit and a syrup.

16. The pharmaceutical composition of claim 14, wherein the orally administrable form is a tablet.

17. A method of treating hyperphosphatemia comprising administering a pharmaceutical composition comprising ferric citrate having an intrinsic dissolution rate of 1.88-4.0 mg/cm$^2$/min and a suitable carrier to a person in need of such treatment.

18. A method of treating metabolic acidosis comprising administering a pharmaceutical composition comprising ferric citrate having an intrinsic dissolution rate of 1.88-4.0 mg/cm$^2$/min and a suitable carrier to a person in need of such treatment.

* * * * *